United States Patent [19]

Jonckers

[11] Patent Number: 5,767,313
[45] Date of Patent: Jun. 16, 1998

[54] METHOD FOR THE PREPARATION OF UREA

[75] Inventor: Kees Jonckers, Susteren, Netherlands

[73] Assignee: DSM N.V., Netherlands

[21] Appl. No.: 652,239

[22] Filed: May 23, 1996

Related U.S. Application Data

[60] Provisional application No. 60/000,326, Jun. 19, 1995.

[30] Foreign Application Priority Data

May 23, 1995 [NL] Netherlands ............ 1000416

[51] Int. Cl.$^6$ ................................ C07C 273/04
[52] U.S. Cl. .................. 564/71; 564/66; 564/67; 564/70
[58] Field of Search .................. 564/66, 67, 70, 564/71

[56] References Cited

U.S. PATENT DOCUMENTS

| | | |
|---|---|---|
| 3,024,280 | 3/1962 | Braun ................... 564/67 |
| 3,686,305 | 8/1972 | Otsuka et al. ........... 564/71 |
| 4,670,588 | 6/1987 | Zardi ................... 564/71 |

FOREIGN PATENT DOCUMENTS

| | | |
|---|---|---|
| 0155735 | 9/1985 | European Pat. Off. . |
| 0213669 | 3/1987 | European Pat. Off. . |
| 59-122452 | 7/1984 | Japan . |

OTHER PUBLICATIONS

Inoue, et al., "Equilibrium of Urea Synthesis. I.", Bulletin of The Chemical Society of Japan, vol. 45, No. 5, pp. 1339–1345 (1972).

Gorlovski, et al., "Equation For Determination Of The Equilibrium Degree of $Co_2$ Conversion During Synthesis of Urea", Journal of Applied Chem. of the USSR 54, 10, pp. 1898–1901 (1981).

Inoue et al., "Equilibrium Of Urea Synthesis. II.", Bulletin of The Chemical Society of Japan, vol. 45, No. 6, pp. 1616–1619 (1972).

*Primary Examiner*—Shailendra Kumar
*Attorney, Agent, or Firm*—Cushman Darby & Cushman IP Group of Pillsbury Madison & Sutro, LLP

[57] ABSTRACT

The present invention relates to a process and apparatus for the preparation of urea, and in particular for urea obtained from ammonium carbamate formulated from carbon dioxide and ammonia at a pressure of about 125 bar to about 350 bar in a urea synthesis solution in a urea reactor. The reactor defines a horizontally arranged condensation zone and contains a heat exchanger. According to this process, $NH_3$ and $CO_2$ are supplied to the reactor and are largely absorbed into the urea synthesis solution. A substantial portion of the heat formed in the condensation is discharged by means of the heat exchanger. The residence time of the urea synthesis solution in the reactor preferably is selected so that at least about 85% of the theoretically obtainable amount of urea is prepared. Thereafter, the urea synthesis solution can be processed into a urea solution or solid urea.

24 Claims, 3 Drawing Sheets

X-X

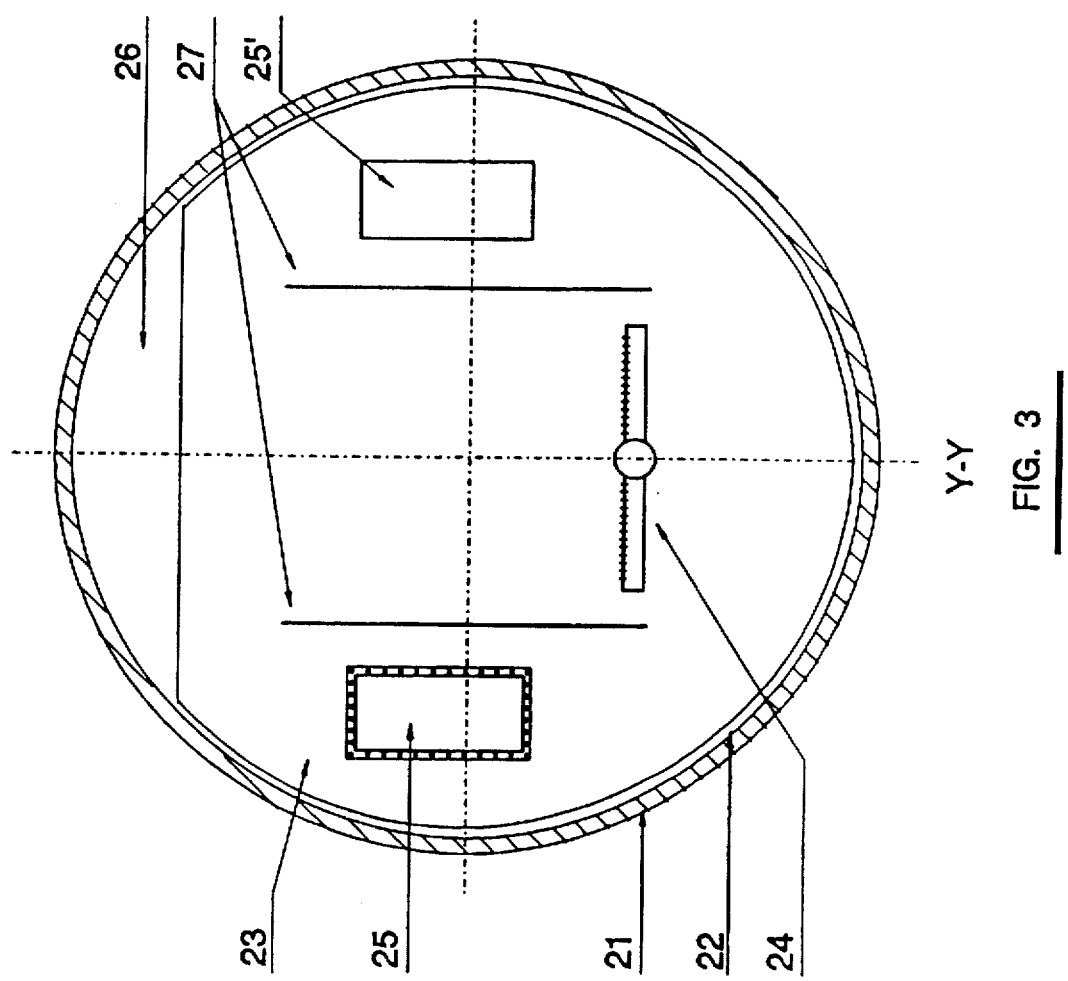
FIG. 3  Y-Y

METHOD FOR THE PREPARATION OF UREA

This application is a continuation of Provisional Application No. 60/000,326 filed Jun. 19, 1995.

BACKGROUND OF THE INVENTION

1. Field of the Invention

The present invention relates to a method for the preparation of urea from ammonia and carbon dioxide.

2. Description of the Related Art

When ammonia and carbon dioxide are introduced into a synthesis zone of a urea plant at a suitable pressure (of for example 125–350 atm.) and a suitable temperature (of for example 170°–250° C.), ammonium carbamate is first formed according to the exothermic reaction:

$$2\ NH_3 + CO_2 \rightarrow H_2N\text{—}CO\text{—}ONH_4 \quad (1)$$

Then urea is formed from the obtained ammonium carbamate through dehydration according to the endothermic equilibrium reaction:

$$H_2N\text{—}CO\text{—}ONH_4 \rightleftharpoons H_2N\text{—}CO\text{—}NH_2 + H_2O \quad (2)$$

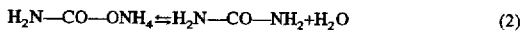

The extent to which the conversion to urea takes place is partly dependent on the temperature and pressure employed, and the amount of excess ammonia used. The reaction product obtained is a solution that consists substantially of urea, water, ammonium carbamate and unbound ammonia. The ammonium carbamate and the ammonia are usually removed from the solution and are in most cases returned to the synthesis zone. The synthesis zone may consist of separate zones for the formation of ammonium carbamate and urea. These zones may, however, also be combined in a single apparatus.

A method that is frequently use for the preparation of urea is described in European Chemical News, Urea Supplement of 17 Jan. 1969, pp. 17–20. According to this method, the urea synthesis solution that is formed in the synthesis zone at a high pressure and temperature is transferred to a stripping zone. There, the synthesis solution is subjected to a stripping treatment at a pressure that is substantially identical to that in the synthesis zone by contacting the solution with a countercurrent of gaseous carbon dioxide while supplying heat, so that the majority of the ammonium carbamate present in the solution decomposes to ammonia and carbon dioxide. These decomposition products are stripped from the solution in gaseous form and are evacuated together with a small amount of water vapor and the carbon dioxide used for the stripping. The gas mixture obtained in the stripping treatment is transferred to a condensation zone, in which the majority of the mixture is condensed and absorbed into an aqueous solution produced by the further treatment of the urea-containing solution. Then both the aqueous ammonium carbamate solution formed in this process and the uncondensed gas mixture are passed from the condensation zone to the synthesis zone for the formation of urea. The heat required for the conversion of ammonium carbamate into urea is here obtained through further condensation of the gas mixture, which releases the heat of condensation.

EP-B-155,735 describes a method for the preparation of urea, and reports that a good synthesis efficiency is obtained and the formation of biuret and the hydrolysis of urea in the stripping treatment remain within acceptable limits. Moreover, the gas mixture obtained in the stripping treatment reportedly is condensed at such a temperature that a considerably smaller heat-exchanging surface area suffices to discharge the heat released, with low-pressure steam of for example 3–5 bar being formed, or steam of a higher pressure, for example of 5–10 bar, being obtained or the heat released being used directly to heat process streams.

According to EP-B-155,735, this is achieved by causing urea to form in the condensation zone as the gas mixture obtained in the stripping operation is condensed. Because of the presence in the condensation zone of relatively large amounts of urea in water, which medium acts as a solvent for the ammonium carbamate formed by the condensation of the gas mixture obtained in the stripping, the heat of condensation and of solution becomes available at a higher temperature level than when this medium is not used. When 30% of the equilibrium amount of urea obtainable has been formed, a heat effect is already clearly noticeable. According to EP-B-155,735 the urea formation is preferably continued to 50–80% of the equilibrium.

According to EP-B-155,735 the condensation zone may be arranged either horizontally or vertically. EP-B-155,735 further mentions that a vertically arranged condensation zone affords the possibility of combining the synthesis zone and the vertical condensation zone in a single apparatus.

JP-A-122,452/84 discloses that a horizontally arranged reactor can be used for urea production. However, JP-A-122,452/84 does not mention combining condensation and synthesis zones. Rather, it describes a method for the preparation of urea, in which a horizontal reactor, and a separate stripper and condenser are used, the gases from the stripper being condensed in the condenser before the condensate is reintroduced into the reactor.

U.S. Pat. No. 3,024,280 describes a method for the preparation of urea, in which a long tubular winding reactor having a total length of approximately 140 m is used. $CO_2$ is added to the urea synthesis solution at various points along the reaction tube while the solution is cooled with the aid of cooling water that passes through the tube jacket.

SUMMARY OF THE INVENTION

It is an object of the present invention is to provide an improved method for the preparation of urea.

It is a further object of the present invention to provide a method for the preparation of urea entails lower investment costs.

To accomplish these and other objects, an embodiment of the present invention provides a method for the preparation of urea, the urea being formed along with ammonium carbonate from a reaction between carbon dioxide and ammonia, preferably at a pressure of about 125 bar to about 350 bar in a urea synthesis solution in a urea reactor. The urea reactor preferably contains a horizontally arranged condensation zone which includes a heat exchanger. According to this method, ammonia ($NH_3$) and carbon dioxide ($CO_2$) are supplied to the reactor and are largely absorbed into a urea synthesis solution. A substantial portion of heat is generated by condensation. This heat is discharged by, for example, means of the heat exchanger. The residence time of the urea synthesis solution in the reactor is selected so that at least about 85% of the theoretically obtainable amount of area is prepared, whereupon the urea synthesis solution can be processed into a urea solution or solid urea.

The method according to the present invention is advantageous in that, among other things, the method can be carried out in a plant with substantially lower investment costs, because of the integration of a heat exchanger/ condenser in a single reactor. Accordingly, fewer apparatuses and pipelines—which must be resistant to high pressure in a highly corrosive environment—are required. Because the present invention can suitably be (and preferably is) practiced with a condenser/heat exchanger part having a horizontal orientation, a smaller (shorter) plant and plant installations are required. This offers further investment benefits and also promotes safety.

Further advantages arrived at by the horizontal orientation of the synthesis and condensation zones of the reactor include better approximations of plug flow, a higher heat transfer coefficient (which decreases the required heat exchange area), a gradual and continuous synthesis zone, and a lower operating pressure without affecting urea composition and the operating temperature. Moreover, this orientation also unexpectedly provides for improved level control, and a pool-condensation that is less sensitive to the $NH_3:CO_2$ feed ratio.

Preferably the entire reactor is designed as a horizontally arranged reactor. As referred to herein, a "horizontal" reactor means a reactor in which the product of the above-mentioned reaction (1) and the condensate move over a substantially horizontal (non-vertical) flow path. The ammonia and carbon dioxide gas fed into the reactor, however, may move over a vertical flow path prior to reaction.

In addition, in accordance with the present invention the supply of the gas phase ($CO_2$ and $NH_3$) can then be distributed across the reactor so that a higher degree of conversion can be achieved, if desired. It is also possible to obtain a particular degree of conversion at a lower pressure. In this manner, the operation of a stripper in the process is simplified. Another advantage of a completely horizontally arranged reactor is that it can be started up in a simple manner, because the entire plant can also be operated when the reactor is only partly filled.

These and other objects, features, and advantages of the present invention will become apparent from the following detailed description when taken in conjunction with the accompanying drawings which illustrate, by way of example, the principles of the present invention.

BRIEF DESCRIPTION OF THE DRAWING

The accompanying drawings illustrate the present invention. In such drawings:

FIG. 3 is a cross-sectional view (along Y—Y in FIG. 1) of the reactor and heat exchanger and, in particular, the condensation zone of the reactor.

DESCRIPTION OF THE PREFERRED EMBODIMENTS

Figure 1:
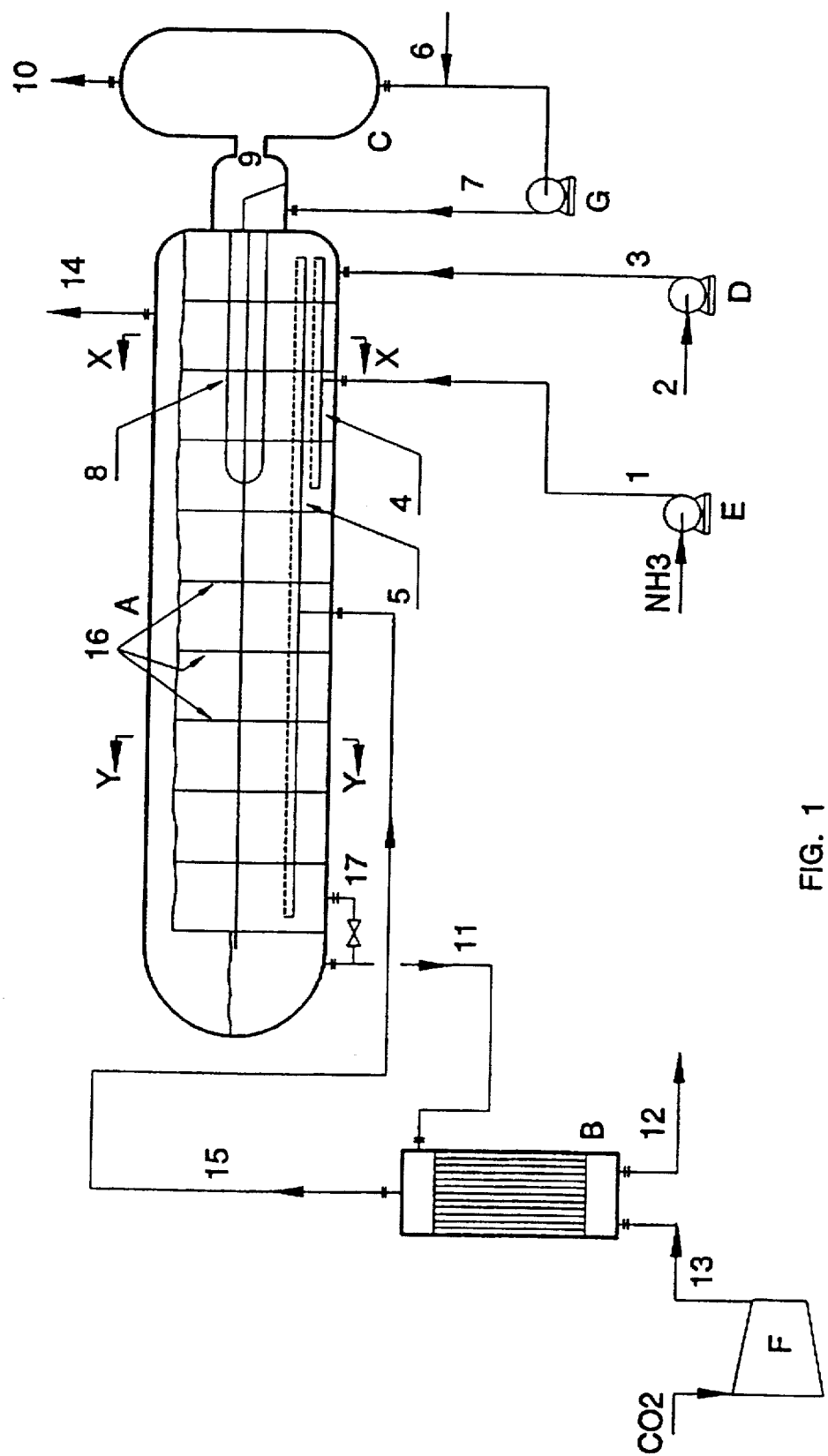
FIG. 1 is a schematic view of a high-pressure section of a urea plant suitable for practicing an embodiment of the process of the present invention.

In accordance with an embodiment of the present invention, a method is provided for preparing urea from ammonium carbamate, which is formulated from carbon dioxide and ammonia. This method comprises the steps of supply $NH_3$ and $CO_2$ to a synthesis zone of a reactor operated at a pressure of about 125 bar to about 350 bar. The reactor includes a synthesis zone an a horizontally arranged condensation zone with a heat exchanger disposed therein. The synthesis and condensation zones preferably overlap completely. Ammonia and carbon dioxide are supplied to the reactor so that the ammonia and the carbon dioxide undergo condensation and are substantially absorbed into a urea synthesis solution, which is maintained in the reactor for a residence time selected so that at least about 85% of a theoretically obtainable amount of urea is prepared. A substantial portion of heat formed from the condensation can thereby be discharged to a fluid passing through the heat exchanger.

The ratio of $NH_3:CO_2$ exiting the reactor is preferably from about 2.85:1 to about 3.5:1, and more preferably 3.1:1.

In accordance with a further embodiment, at least a portion of the carbamate is removed from the reactor and decomposed in a stripping zone to form carbamate decomposition products. These products are then passed to the reactor for condensation in the condensation zone, with a substantial portion of heat formed from the condensation being discharged to the fluid passing through the heat exchanger.

The theoretically obtainable amount of urea is determined by the thermodynamic position of the equilibrium and is dependent on for example the $NH_3/CO_2$ ratio, the $H_2O/CO_2$ ratio and he temperature. This theoretical obtainable amount (x) can be calculated with the aid of the models as described in, for example, S. Inoue et al., Bull. of the Chem. Soc. of Japan 1972, Vol. 45, pp. 1339–1345, and D. M. Gorlovskii et al., J. Applied Chem. of the USSR (1981), Vol. 54, pp. 1898–1901, which are incorporated herein by reference. From these models, the following equation (as reported in Gorlovskii et al.) is derived for calculating (x):

$$x = 94.31L - 139.9L^{0.5} - 4.284L^2 - 26.09W +$$
$$2.664WL + 1.54t - 0.09346tL - 10^{-5} \times 1.059t^3 - 97.82$$

wherein t is temperature (°C.), and L and W are the molar ratios of $NH_3:CO_2$ and $H_2O:CO_2$, respectively, in the reaction mixture.

Preferably the residence time of the urea synthesis solution is selected so that at least about 90% of the theoretically obtainable amount of urea is prepared, and more preferably more than about 95%.

The conversion of carbamate into urea and water in the reactor can be effected by ensuring that the residence time of the reaction mixture in the reactor is sufficiently long. The residence time will generally be more than about 10 min., and preferably more than about 20 min. On the other hand, the residence time also will generally be shorter than about 2 hours, and preferably shorter than about 1 hour. At a higher reactor temperature and pressure, a short residence time will often suffice to obtain a high degree of conversion.

The pressure in the reactor is preferably between about 130 bar and about 210 bar, and the temperature is preferably between about 170° C. and about 200° C.

The reactor is usually designed to generally have the shape of a wide pipe with a diameter of between about 1 m and about 5 m, preferably between about 2 m and about 4 m. The length of the reactor is generally between about 5 m and about 40 m, preferably between about 10 m and about 25 m.

The reactor is generally provided with means that ensure that the liquid flows through the reactor substantially in plug flow. To this end, the reactor is provided with, for example, a structured packing (in one or more places) or with partitions, which divide the reactor into compartments. The compartments are somewhat similar in appearance to "continuously stirred tank reactors" (CSTRs) arranged in series. Although reference is made herein to CSTRs and compartments, these terms are included in the interest of brevity and are not intended to restrict the invention thereto.

The number of compartments or CSTRs in the reactor arranged in series is generally greater than 2 and preferably greater than 5. In general the number of compartments (CSTRs) will be smaller than 40, preferably smaller than 20.

The compartments are preferably defined by substantially vertical partitions. The partitions preferably have a surface area that is at least about 50% of the area of the vertical cross-sectional area of the horizontally placed reactor, and more preferably at least about 85% of the vertical cross-sectional area of the reactor. Preferably the area of the partitions is at most about 98% of the vertical cross-sectional area of the horizontally placed reactor.

Preferably turbulence in the reactor compartments is provided by introducing a gas via a distributing device, for example via a pipe having holes therein, the pipe being disposed at or near the bottom of the reactor. Ammonia, carbon dioxide and/or inert gas can suitable be used as the introduced gas.

The liquid ammonia preferably is introduced into the reactor in the portion thereof that also contains the condenser/heat exchanger. The $CO_2$ and any gaseous ammonia present preferably are fed into all the compartments of the reactor, but a larger proportion, preferably more than about 60%, is preferably fed to the portion of the reactor that contains the condenser/heat exchanger. Inert gas can be fed into all or any combination of the compartments. The inert gas will often be present in recycle streams, together with $CO_2$ and gaseous ammonia.

The gas phase that is fed to the reactor can be divided optimally between the series-arranged CSTRs by suitable dimensioning of the distributing device. This makes it possible, for example, to minimize the amount of non-condensable gases in the off-gas of the last CSTRs. In this manner, the vapor pressure of the condensable components is maximized in that part of the reactor where the thermodynamically determined equilibrium is approached. This means that, at a given total pressure (i.e., the sum of the vapor pressure of the condensable components plus the pressure of the non-condensable components), the temperature in this part of the reaction zone is maximized, as a result of which a higher degree of conversion is obtained. Alternatively, this arrangement is also suitable for minimizing the total pressure at a given temperature, so that for example a better performance of the stripping operation can be realized.

The heat or energy that is discharged in the heat exchanger of the reactor is generally more than about 125 kWh per ton of urea produced. In general, the energy will be less than about 800 kWh per ton of urea produced.

The heat released in the reaction can then be transferred to and discharged by water or other fluid that is passed through tubes of the heat exchanger and is in the process converted into low-pressure steam of preferably about 3 bar to about 10 bar, and more preferably about 4 bar to about 7 bar. The heat can also be discharged by passing a process stream that is to be heated through it, for example a urea solution that is to be evaporated at about 2 bar to about 8 bar or a urea solution that is to be expanded at about 15 bar to about 40 bar. The heat exchanger preferably is disposed in the upstream (first) half of the reactor. Although condensation occurs over the complete length of the reactor, about 80% of the condensation preferably occurs in the first half of the reactor, with the remaining about 20% occuring in the second half. In this manner, the rate of reaction (synthesis), which occurs over the complete length of the reactor, increases over the length of the reactor.

Preferably the condensation zone and heat exchanger of the reactor are designed as a so-called submerged condenser, in which a portion of the gaseous mixture to be condensed, the ammonia, and dilute carbamate solution are fed into the shell side of a shell-and-tube heat exchanger. The heat of solution and condensation released is transferred to and discharged by a medium flowing through the tubes, for example water, which is converted into low-pressure steam.

The method according to the invention can be used in a so-called conventional urea process, but is preferably used in a stripping process as described in ECN Urea Supplement of 17 Jan. 1969, pp. 17–20, in Hydrocarbon Processing of July 1975, pp. 102–104, or in Nitrogen, May–June 1990, pp. 22–29, which are incorporated herein by reference. In this preferred embodiment of the method according to the invention the urea synthesis solution formed in the reactor is fed to a stripper, where carbamate is decomposed, whereupon the gases obtained are returned to the reactor.

The decomposition of the ammonium carbamate present in the urea synthesis solution is generally effected by supplying heat. If only heat is supplied, this process is also known as thermal stripping. However, the decomposition preferably is effected by stripping with the aid of a stripping gas in countercurrent to the urea synthesis solution, with addition of heat. Ammonia, carbon dioxide, and an inert gas, alone or in any combination, can be used as the stripping gas.

The stripping operation can be carried out at a pressure that is the same as the synthesis pressure or at a slightly higher or lower pressure. Preferably substantially the same pressures are used in the reactor and in the stripping zone, since this makes it possible to return the gases formed in the stripping zone to the reactor in a non-complex manner.

In another embodiment of the present invention the gases from the stripper are used to convert water into steam or to heat a process liquid in a first heat exchanger disposed outside the reactor, after which the partially condensed gases are sent to the reactor according to the invention. In this manner, at most about 70% and preferably at most about 50% of the energy to be discharged from condensation is discharged in this first heat exchanger; correspondingly, at least about 30%, and preferably more than about 50%, of the heat of condensation is discharged in the heat exchanger of the reactor. This embodiment is advantageous when, for example, a process stream needs to be heated (for example a urea solution to be expanded) and the generation of steam as a by-product is desirable.

A particularly advantageous embodiment of the present invention involves preparing the urea in a reactor with a condensation zone and a heat exchanger, in which the gases from the stripper are returned directly to the condensation zone. In this case all of the energy to be discharged is discharged in and transferred to the heat exchanger of the reactor. This is particularly preferable because of the simplicity, and hence inexpensive nature of the design.

Preferably carbon dioxide ($CO_2$) is used as the stripping gas so that the stripping gas is hence used as the $CO_2$-containing gas that is fed to all the reactor's compartments. Besides $CO_2$, this stripping gas contains $NH_3$ and inert gas. In addition to all the extra liquid ammonia to be supplied, preferably more than about 60% of this stripping gas, in particular more than about 70%, is fed to the condenser zone of the reactor.

The present invention is illustrated by the following figures and the examples, without being limited thereto.

As shown in FIG. 1, A represent a reactor with a condensation zone and a heat exchanger, B a stripping zone, C a steam reservoir, and D, E, F and G pumps or compressors.

Pump E supplies compressed liquid ammonia to the reactor's condensation zone via conduit (1) and via a pipe (4) provided with openings. A carbamate solution that has been obtained elsewhere in the process, in particular by washing off-gases with an aqueous solution obtained in the evaporation of the urea solution, is introduced into the reactor (1) via conduits (2) and (3) by means of pump D. A gaseous mixture containing ammonia and carbon dioxide is introduced into the liquid via a pipe (5) provided with openings. This gaseous mixture—supplied via pipe (15)—is obtained by subjecting the urea synthesis solution formed in the reactor (A) to a stripping treatment in the stripping zone (B), with the addition of heat and in countercurrent contact to a stripping gas, for example carbon dioxide, supplied via pipe (13). The pressures in the reactor (A) and the stripping zone (B) are the same in the embodiment shown, for example about 140 bar. The pressures in these zones may, however, differ from one another. The dimensions of the reactor (A) are selected so that the residence time of the reaction mixture in this reactor is sufficiently long to ensure that at least about 85% of the theoretically possible amount of urea is formed in the reactor. The reactor (A) is provided with partitions (16) (or (23) in FIGS. 2 and 3) which divide the reactor into compartments. The last partition (i.e., located at the far left of the reactor depicted in FIG. 1) has an aperture at the upper portion thereof only to enable the level of the condensate in the last compartment to be controlled. At startup the penultimate and last compartments must then be (temporarily) connected to one another via a bypass pipeline (17), so that a urea synthesis solution can already be discharged when the reactor is half full.

The heat that is released in the reactor (A) is discharged with the aid of water, which is supplied via conduit (6), which is passed through the heat exchanger (8) installed in the reactor (A) by means of pump G via conduit (7). The water is converted into low-pressure steam in that process. The steam formed is sent to steam reservoir C via conduit (9) and is discharged therefrom via conduit (10) to a low-pressure steam-consuming installation (not shown) which can be, for example, the recycling and/or evaporation section. Instead of discharging the heat as a steam formation, it is also possible to pass a process stream that needs to be heated, for example an aqueous urea solution that is to be concentrated, such as stream (12), through the cooling elements.

The inert gases which contain ammonia and $CO_2$ are discharged from the reactor (A) via outlet (14). $NH_3$ and $CO_2$ are removed from these gases in a known manner. The urea synthesis solution passes from the reactor (A) via conduit (11) to the stripping zone (B). The stripped urea synthesis solution is discharged via stream (12) and can be further processed to an aqueous urea solution and concentrated in a known manner, where upon the concentrated solution is optionally converted into solid urea.

Figure 2:
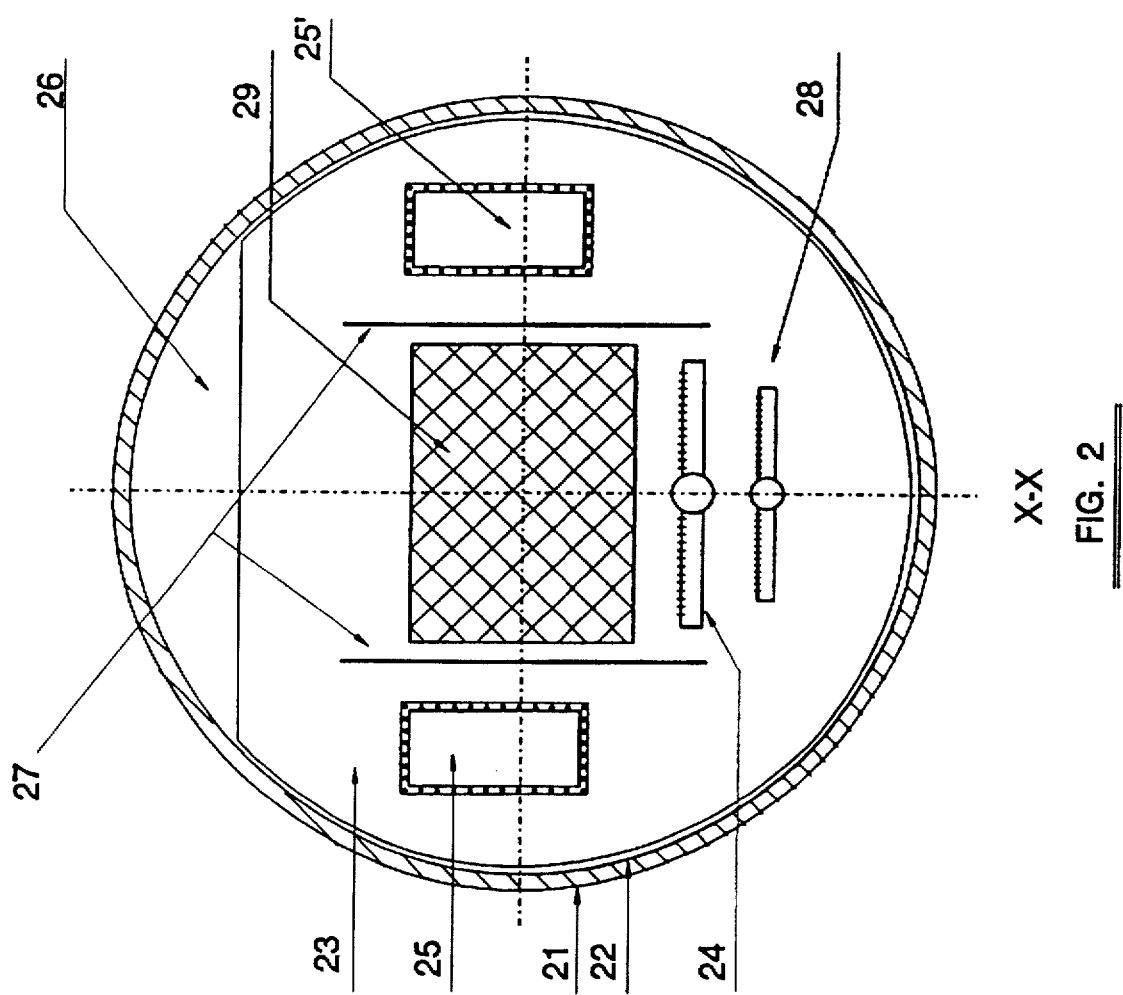
FIG. 2 is a cross-sectional view (along X—X in FIG. 1) of a reactor suitable for urea plant of FIG. 1 and, in particular, the condensation zone of the reactor.

In FIGS. 2 and 3, which represent cross-sections of the reactor A, (21) represents the reactor wall. For practical reasons there can be an opening (22) defined between the partitions (23) which divide the reactor into compartments and the wall (21). The gas from the stripper is introduced into the reactor A through the distributing device (24). For practical reasons there are manholes (25) and (25') in each partition. When the reactor is in operation, the manholes may be open or closed, depending on the desired throughput of the urea synthesis solution. The manholes in the partitions near the heat exchanger (29) are preferably closed, while each of the remaining partitions preferably has only one manhole open, with the open manholes being alternated a staggered fashion so that a zigzag liquid stream is obtained. The top side of a partition (23) defines an opening (26) as a gas discharge area. The partitions may be provided with vertical baffle partitions (27), which are however not essential. In FIG. 3 ammonia is introduced into the reactor by means of the distributing device (28) at the level of the condenser/heat exchanger and the heat exchanger is represented as (29).

A method for the preparation of urea is disclosed in NL 1,000,416, filed May 23, 1995, which is incorporated herein by reference.

The following non-limiting examples serve to explain embodiments of the present invention in more detail.

EXAMPLE

A plant with a high-pressure synthesis unit as shown in FIG. 1 was used to produce 70 tons of urea per hour. The pressure was 144 bar; under these conditions the degree of conversion in the reactor was 95% relative to the theoretical equilibrium. In the heat exchanger 78.7 tons of steam of 4.5 bar (148° C.) was produced per hour from 78.7 tons of condensate of 175° C.; this corresponds to some 600 kWh per ton of urea.

The streams through the pipelines were as follows.

| | Amounts in tons/hour | | | | | | |
|---|---|---|---|---|---|---|---|
| Component | 1 | 2 | 11 | 12 | 13 | 14 | 15 |
| Urea | | | 75.2 | 70.0 | | | |
| $NH_3$ | 39.7 | 20.8 | 62.9 | 8.7 | | 12.1 | 57.1 |
| $CO_2$ | | 17.1 | 35.8 | 11.7 | 51.3 | 5.4 | 79.2 |
| $H_2O$ | | 9.7 | 36.5 | 30.2 | | 0.6 | 4.8 |
| $N_2$ | | | | | 1.3 | 1.3 | 1.3 |
| $O_2$ | | | | | 0.2 | 0.2 | 0.2 |
| TOTAL | 39.7 | 47.6 | 210.3 | 120.5 | 52.9 | 19.7 | 142.7 |
| Temp. (°C.) | 20 | | 186 | 173 | 120 | 176 | 187 |

The stripped urea synthesis solution obtained from pipeline (12) was further processed into solid urea in a manner known to those skilled in the art.

Although the present invention has been described in detail with reference to its presently preferred embodiments, it will be understood by those of ordinary skill in the art that various modifications and improvements to the present invention are believed to be apparent to one skilled in the art. Accordingly no limitation upon the invention is intended, except as set forth in the appended claims.

What is claimed is:

1. A method for the preparation of urea, the urea being formed along with ammonium carbamate from at least carbon dioxide and ammonia at a pressure of from about 125 bar to about 350 bar, said method comprising the steps of:

providing a reactor comprising a horizontally arranged, combination synthesis and condensation zone, the combination synthesis and condensation zone containing a heat exchanger;

supplying ammonia and carbon dioxide to the reactor and condensing and absorbing at least a portion of the ammonia and the carbon dioxide into a urea synthesis solution contained in the combination synthesis and condensation zone, said condensing and absorbing steps occurring in a continuous manner over a length of the combination synthesis and condensation zone;

discharging a substantial portion of heat released during said condensing step to a heat exchanging fluid passing through the heat exchanger;

synthesizing urea and ammonium carbamate from the ammonia and the carbon dioxide in a continuous manner over the length of the combination synthesis and condensation zone; and maintaining the urea synthesis solution in the reactor for a residence time selected so that at least about 85% of a theoretically obtainable amount of urea is prepared, wherein a first portion of the reactor where the ammonia and the carbon dioxide are condensed and absorbed into the urea synthesis solution and a second portion of the reactor where the urea and the ammonium carbamate are synthesized completely overlap each other.

2. A method according to claim 1, wherein the residence time of the urea synthesis solution is selected so that at least about 90% of the theoretically obtainable amount of urea is prepared.

3. A method according to claim 1, wherein the reactor is arranged horizontally.

4. A method according to claim 3, further comprising a step of flowing the urea synthesis solution through the combination synthesis and condensation zone substantially in plug flow.

5. A method according to 2, wherein the reactor has a pipe shape, with a diameter of between about 1 m and about 5 m and a length of between about 5 m and about 40 m.

6. A method according to claim 5, further comprising providing the combination synthesis and condensation zone of the reactor with a structured packing or partitions which divide the reactor into compartments.

7. A method according to claim 6, further comprising a step of introducing gas into the compartments to generate turbulence.

8. A method according to claim 1, further comprising a step of supplying liquid ammonia to a portion of the combination synthesis and condensation zone containing the heat exchanger.

9. A method according to claim 1, wherein said supplying step further comprises supplying at least about 60% of the carbon dioxide to a portion of the combination synthesis and condensation zone containing the heat exchanger.

10. A method for the preparation of urea, the urea being formed along with ammonium carbamate from at least carbon dioxide and ammonia at a pressure of about 125 bar to about 350 bar, said method comprising the steps of:

providing a reactor comprising a horizontally arranged, combination synthesis and condensation zone, the combination synthesis and condensation zone containing a heat exchanger;

supplying ammonia and carbon dioxide to the reactor and condensing and absorbing at least a portion of the ammonia and the carbon dioxide into a urea synthesis solution contained in the combination synthesis and condensation zone, said condensing and absorbing steps occurring in a continuous manner over a length of the combination synthesis and condensation zone;

synthesizing urea and ammonium carbamate from the ammonia and the carbon dioxide in a continuous manner over the length of the combination synthesis and condensation zone; and maintaining the urea synthesis solution in the reactor for a residence time selected so that at least about 85% of a theoretically obtainable amount of urea is prepared;

removing at least a portion of the carbamate from the reactor and decomposing the carbamate in a stripping zone to form carbamate decomposition products;

passing the carbamate decomposition products to the reactor and condensing at least a portion of the carbamate decomposition products in the combination synthesis and condensation zone;

discharging a substantial portion of the heat released during said condensing steps to a heat exchanging fluid passing through the heat exchanger, wherein a first portion of the reactor where the ammonia and the carbon dioxide are condensed and absorbed into the urea synthesis solution and a second portion of the reactor where the urea and the ammonium carbamate are synthesized completely overlap each other.

11. A method according to claim 10, wherein said step of decomposing the carbamate in a stripping zone to form carbamate decomposition products further comprises obtaining a $CO_2$-containing gas in the stripping zone, and further wherein said step of passing the carbamate decomposition products to the reactor comprises returning the $CO_2$-containing gas to the combination synthesis and condensation zone of the reactor.

12. A method according to claim 11, wherein heat that is discharged in the heat exchanger of the reactor amounts to more than about 125 kWh per ton of the urea produced.

13. A method according to claim 10, wherein the residence time of the urea synthesis solution is selected so that at least about 90% of the theoretically obtainable amount of urea is prepared.

14. A method according to claim 10, wherein the reactor is arranged horizontally.

15. A method according to claim 14, further comprising a step of flowing the urea synthesis solution through the combination synthesis and condensation zone substantially in plug flow.

16. A method according to 13, wherein the reactor has a pipe shape, with a diameter of between about 1 m and about 5 m and a length of between about 5 m and about 40 m.

17. A method according to claim 16, further comprising providing the combination synthesis and condensation zone of the reactor with a structured packing or partitions which divide the reactor into compartments.

18. A method according to claim 17, further comprising a step of introducing gas into the compartments to generate turbulence.

19. A method according to claim 10, further comprising a step of supplying liquid ammonia to a portion of the combination synthesis and condensation zone containing the heat exchanger.

20. A method according to claim 10, wherein said supplying step further comprises supplying at least about 60% of the carbon dioxide to a portion of the combination synthesis and condensation zone containing the heat exchanger.

21. A process according to claim 1, wherein a first half of the length of the combination synthesis and condensation zone comprises the heat exchanger and an inlet for supplying the ammonia and the carbon dioxide to the combination synthesis and condensation zone, wherein a second half of the length of the combination synthesis and condensation zone comprises an outlet for discharging the urea synthesis solution therefrom, and wherein about 80% of the ammonia and the carbon dioxide condensed during said step of condensing and absorbing the ammonia and the carbon dioxide into the urea synthesis solution is condensed over the first half of the length of the combination synthesis and condensation zone.

22. A process according to claim 21, wherein a rate of said synthesis step increases over the length of the combination synthesis and condensation zone from the inlet to the outlet.

23. A process according to claim 10, wherein a first half of the length of the combination synthesis and condensation zone comprises the heat exchanger and an inlet for supplying the ammonia and the carbon dioxide to the combination synthesis and condensation zone, wherein a second half of the length of the combination synthesis and condensation zone comprises an outlet for discharging the urea synthesis solution therefrom, and wherein about 80% of the ammonia and the carbon dioxide condensed during said step of condensing and absorbing the ammonia and the carbon dioxide into the urea synthesis solution is condensed over the first half of the length of the combination synthesis and condensation zone.

24. A process according to claim 23, wherein a rate of said synthesis step increases over the length of the combination synthesis and condensation zone from the inlet to the outlet.

* * * * *